(12) United States Patent
Seex et al.

(10) Patent No.: US 9,289,248 B2
(45) Date of Patent: Mar. 22, 2016

(54) ASSEMBLY WITH OFFSET ALLOWING VERTEBRAL DISTRACTION BY AXIAL ROTATION OF A CONCENTRIC MEMBER

(76) Inventors: Kevin Seex, New South Wales (AU); Donald Fry, New South Wales (AU)

(*) Notice: Subject to any disclaimer, the term of this patent is extended or adjusted under 35 U.S.C. 154(b) by 438 days.

(21) Appl. No.: 13/505,889

(22) PCT Filed: Nov. 6, 2010

(86) PCT No.: PCT/AU2010/001474
§ 371 (c)(1),
(2), (4) Date: Aug. 20, 2012

(87) PCT Pub. No.: WO2011/054048
PCT Pub. Date: May 12, 2011

(65) Prior Publication Data
US 2012/0310249 A1    Dec. 6, 2012

(30) Foreign Application Priority Data
Nov. 6, 2009   (AU) .................... 2009905425

(51) Int. Cl.
*A61B 17/60* (2006.01)
*A61B 17/70* (2006.01)
*A61B 17/02* (2006.01)
*A61B 17/88* (2006.01)
(Continued)

(52) U.S. Cl.
CPC ............ *A61B 17/708* (2013.01); *A61B 17/025* (2013.01); *A61B 17/8866* (2013.01); *A61B 17/86* (2013.01); *A61B 2017/0256* (2013.01); *A61F 2/4611* (2013.01)

(58) Field of Classification Search
CPC .............. A61B 17/025; A61B 2017/0256; A61B 2017/0262; A61B 17/60; A61B 17/66; A61B 2017/681
USPC ............................ 606/86 R, 99, 104, 105
See application file for complete search history.

(56) References Cited

U.S. PATENT DOCUMENTS

| 4,658,809 A | 4/1987 | Ulrich et al. |
| 6,017,342 A | 1/2000 | Rinner |

(Continued)

FOREIGN PATENT DOCUMENTS

WO    WO 0185033 A2 * 11/2001 ............. A61B 17/02

OTHER PUBLICATIONS

Written Opinion of the International Searching Authority for PCT/AU2010/001474 Dated Dec. 23, 2010.
(Continued)

*Primary Examiner* — Anu Ramana
(74) *Attorney, Agent, or Firm* — Nicholas B. Trenkle; Stites & Harbison PLLC

(57) ABSTRACT

An assembly for distraction of spinal vertebrae and which can optionally accommodate retraction blades. The assembly includes a pair of pins each having a first end adapted for vertebral bone engagement and a second end. A pair of sleeves respectively and concentrically engage said pins. A frame includes respective openings which receive the pins and a first end of each said sleeves. The first end of each said sleeve including a portion offset relative to a longitudinal axis of said sleeve such that when the first end of each said pins is anchored in bone, axial rotation of each said sleeves enables said first end of each said pins to move between a first position in which said vertebral bones are not distracted and a second position in which said vertebral bones are distracted.

18 Claims, 3 Drawing Sheets

(51) Int. Cl.
*A61B 17/86* (2006.01)
*A61F 2/46* (2006.01)

(56) References Cited

U.S. PATENT DOCUMENTS

| | | | |
|---|---|---|---|
| 6,113,599 A * | 9/2000 | Landsberger | 606/60 |
| 6,669,699 B2 | 12/2003 | Ralph et al. | |
| 6,712,825 B2 | 3/2004 | Aebi et al. | |
| 6,743,231 B1 | 6/2004 | Gray et al. | |
| 6,749,613 B1 | 6/2004 | Conchy et al. | |
| 7,029,472 B1 * | 4/2006 | Fortin | 606/60 |
| 2002/0107519 A1 * | 8/2002 | Dixon et al. | 606/61 |
| 2008/0114367 A1 | 5/2008 | Meyer | |
| 2009/0306671 A1 | 12/2009 | McCormack et al. | |

OTHER PUBLICATIONS

International Preliminary Report on Patentability for PCT/AU2010/001474 Dated May 8, 2012.

International Search Report for PCT/AU2010/001474 dated Jan. 28, 2011.

\* cited by examiner

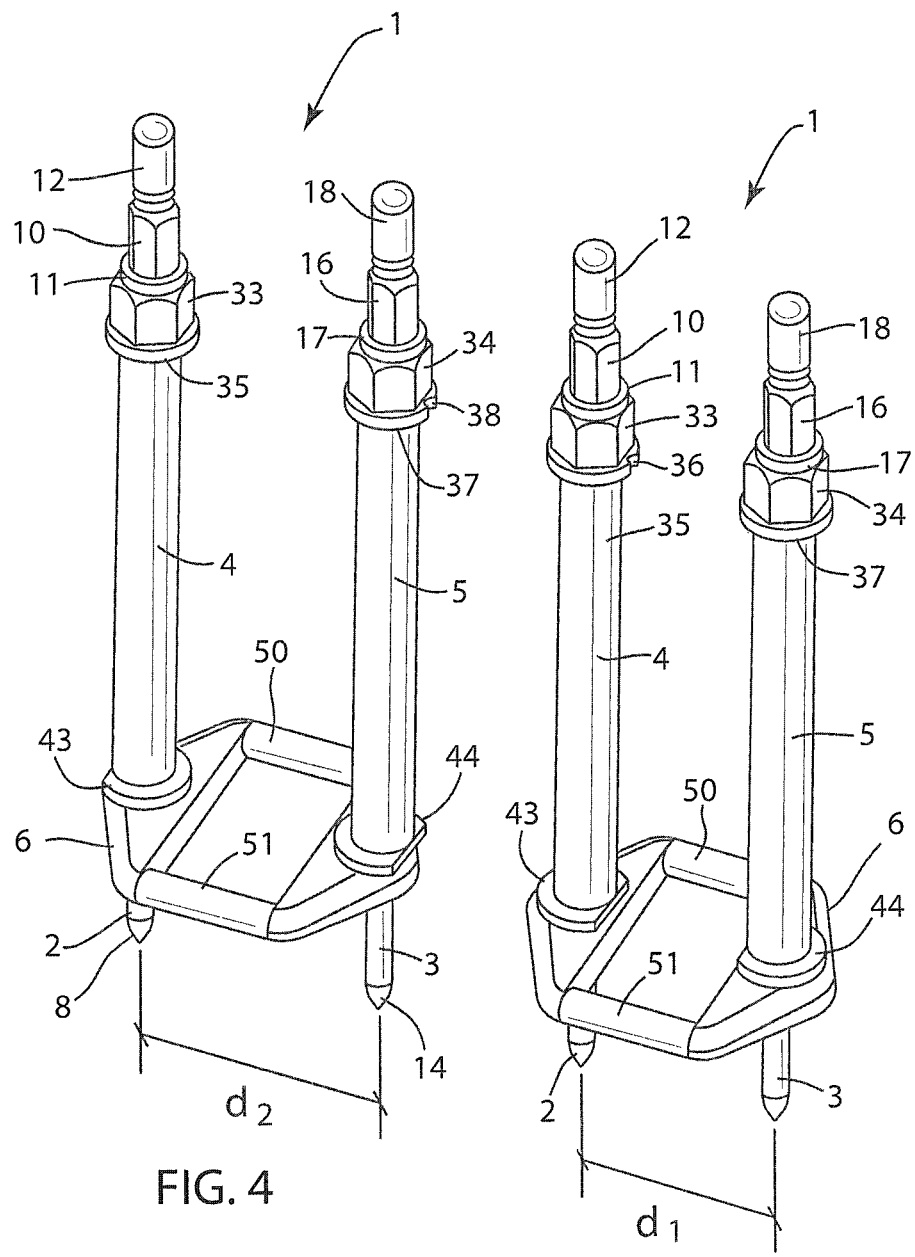

ASSEMBLY WITH OFFSET ALLOWING VERTEBRAL DISTRACTION BY AXIAL ROTATION OF A CONCENTRIC MEMBER

BACKGROUND

The present invention relates to distraction assemblies for use in surgery including, but not limited to spinal surgery. The invention also relates to an assembly which performs the function of distraction optimising mechanical advantage and efficiency during the distraction step. The invention further relates to a distraction assembly which allows vertebral distraction by axial rotation of a sleeve which retains an anchor pin fixed in bone.

PRIOR ART

There are in existence a number of assemblies used for distraction of vertebral bone to facilitate spinal and particularly cervical spine surgery.

The most commonly performed anterior cervical procedure is an intervertebral fusion procedure that typically involve the steps of removing a portion or all of the affected disc material, spreading apart adjacent vertebrae with a distracter, and inserting an implant bone or cage or prosthetic disc into the space previously occupied by the removed disc material. This procedure can be done either from the front of the patient (anterior interbody fusion) or in the lumbar spine from the back (posterior interbody fusion).

By way of an example of a known device, U.S. Pat. No. 6,669,699 discloses a distraction instrument for use in anterior cervical fixation surgery. An intervertebral distraction tool has a clamshell head with upper and lower halves, each having a curved outer surface and a flat inner surface. The distal side of the head is hinged so that the head opens and closes from the proximal side of the head.

In another example U.S. Pat. No. 6,743,231 discloses temporary spinal fixation apparatuses and methods for temporarily fixing the relative position of spinal implant assemblies until a permanent fixation position is determined. The disclosed apparatuses and methods enhance the ease of placement of spinal implant assemblies and facilitates the accuracy of positioning of the spinal vertebrae. This apparatus can reduce the number of steps needed to perform spinal surgery and can decrease the likelihood of post-operative complications.

In another example U.S. Pat. No. 6,017,342 discloses a compression and distraction instrument having two pivotally connected handles. Jaw portions engage objects, such as human bone, for purposes of maneuvering. A control screw connects with the handles, through a mechanical advantage arrangement, and the screw pivots the jaw portions for the engagement of the objects. There is an anti-friction connection between the screw and the handles, for accurate and precise movement of the jaws.

In another example U.S. Pat. No. 6,712,825 of Mar. 30, 2004 discloses a spinal disc space distracter for separating adjacent elements, such as vertebrae. The distracter preferably has a scissors-type distracting mechanism, either in a simple scissors or double-acting scissors configuration. The distracter includes blades that are removable from the jaws of the distracter such that different blades may be used depending on the patient and situation with which the distracter is to be used. The jaws include a mating fixture and the blades include a mating portion for removable association with the mating fixture. This distracter has a scissor-like configuration with a pair of handles pivotally connected together. A distracter jaw is coupled to a distal end of each handle such that movement of the handles together draws the jaws apart to separate the vertebrae being treated.

Typically according to one method, cervical distraction of vertebrae involves the use of pins temporarily fixed to the vertebrae to be distracted. Generally two pins are used one above and one below a disc or vertebral body of interest. Traditionally in a Caspar system these pins have only been used for distraction purposes via sliding tubes that fit axially over the pins and connect to an associated distraction mechanism. According to one aspect the role of the pin has been expanded to perform one or more of the following roles. The pin acts as x-ray marker to estimate a midline of a spine for cage or prosthetic disc replacement. The known and commonly used Caspar type distracter is then secured to the spine. There is however known use of distracter tubes that each slide over respective pins and which are secured to the pins via a screw applied at a threaded region. This however, does not have snug hex or square fit at a base of the pin but is round and transfers distraction forces along a length of a round pin. This does not provide optimal load transfer to the spinal vertebrae where distraction is required but rather applies the load at a rotation point disposed at a moment arm distance from the required load application site. The known techniques for distraction force application apply combined bending and shear forces to the pins which must be transferred down the pin to its point of engagement with the vertebrae. A mechanical advantage during distraction is provided the closer the load is applied to the vertebrae due to a reduced moment arm and elimination of a bending moment on the pins.

In order to achieve fusion it is known that compression of fractured bones or compression of interbody graft improves bone fusion. This is known as Wolf's law. It would be an advantage if the same method for achieving distraction could also be used to apply compression forces to the vertebrae. If this compression could be applied after insertion of interbody graft or cage then this position with the bones applying compression forces to the graft could then be maintained by fixation of the positioned vertebrae with screws and or plates.

There remains an on going need to improve the known distraction assemblies and more particularly to place the distraction load as close possible to the vertebral bone to minimise or eliminate combined shear and bending forces in distracter pins at the point where load is required to effect distraction. Simplifying the mechanism and reducing the number of steps required to achieve and maintain distraction would be advantageous.

INVENTION

The present invention in one form provides improvements in distraction assemblies in applications including, but not limited to spinal surgery and which provides a useful alternative to the known distracters. The invention also provides an assembly which performs the function of distraction optimising mechanical advantage and efficiency in distraction.

The invention further provides distraction of vertebrae using distraction pins and co operating sleeves so that a mechanical advantage in distraction is achieved optimising efficiency in distraction.

Although the invention will be described primarily with reference to its surgical applications it will be recognised by persons skilled in the art that the invention has wider applications in distraction. Distraction can be taken to include that process used in surgery in which vertebra are displaced generally along a longitudinal axis of the spine to increase the space between them to enable performance of a surgical procedure such as but not limited to removal and replacement of a disc.

In the embodiments to be described below there exist the following common features:
1. A means for fixation to bone
2. A retractor anchorage
3. A means to operate pins to facilitate distraction of vertebrae This invention in all its forms has application whenever bone fixation is available principally in spinal and orthopedic surgery but also other surgical disciplines.

It is, an object of the present invention to provide an improved distraction assembly which may be used in conjunction with retraction blades for retracting wound margins and which provides optimal anchorage for such blades.

It is further an object of the present invention to provide an assembly that efficiently and simply manages the insertion of a distracter for receiving retractor blades. Other objects of the present invention not explicitly stated will be set forth and will be more clearly understood in conjunction with the descriptions of the preferred embodiments disclosed hereafter.

In its broadest form the present invention comprises:
a distracter assembly including;
at least one pin which is capable of anchorage in bone via a first end,
at least one member which is mountable concentrically with said at least one pin;
a base member which receives the at least one pin and retains the at least one concentric member;
the at least one concentric member including a surface which co operates with a surface on the base member such that upon rotation of the at least one concentric member, the at least one pin displaces thereby displacing the bone in which the at least one pin is anchored.

In another broad form the present invention comprises:
a distracter assembly including pins which anchor to vertebral bone, sleeves which receive said pins concentrically, wherein axial rotation of the sleeves causes the pins to move in a manner which displaces the vertebra to which the pins are attached.

Preferably the concentric sleeves include an offset portion which allows the pins to undergo arcuate displacement upon rotation of the concentric sleeves which translates into axial displacement of vertebrae.

In another broad form the present invention comprises:
an assembly for distraction of spinal vertebrae; the assembly including;
a pair of pins each having a first end adapted for bone engagement and a second end;
a pair of sleeves which respectively and concentrically engage said pins;
a frame including respective openings which receive a first end of each said sleeves;
the first end of each said sleeve including a portion offset relative to a longitudinal axis of said sleeve such that when the first end of each said pins is anchored in bone, axial rotation of each said sleeves causes said first end of each said pins to move between a first position in which said vertebral bone is not distracted and a second position in which said vertebral bone is distracted.

According to a preferred embodiment, the offset portion of each sleeve engages said openings in said frame such that a longitudinal axis of each pin is offset from an axis through said offset portion.

According to a preferred embodiment, as each said sleeve is rotated, the first end of each pin defines an arc of rotation about the axis through said offset portion.

According to a preferred embodiment the frame includes means to receive and retain at least one retractor blade. Said means to receive retractor blades comprises spaced apart bridging members.

According to a preferred embodiment, the sleeves concentrically engage said pins;

According to a preferred embodiment the assembly further comprising means to apply a distraction force to said pins via said sleeves;

In another broad form the present invention comprises:
an assembly allowing distraction of adjacent spinal vertebrae the assembly comprising;
a pair of anchor pins each having a first end which is capable of engagement with respective vertebrae,
a pair of sleeves which respectively and concentrically engage said anchor pins;
a frame including respective openings which each receive one of said sleeves via an offset portion of said sleeves; wherein the offset portion of each sleeve locates the longitudinal axis through each said pins in an offset position relative to a central axis through said offset portion of each sleeve thereby the first ends of the pins to move between a first position of minimum pin separation in which the vertebrae are in their natural undistracted position and a second position of maximum pin separation in which the vertebrae are distracted to a maximum extent.

According to one embodiment the pins may located in any position along an arc of rotation between said first and second positions depending upon the degree of distraction of the vertebra required.

Preferably axial rotation of the sleeves translates to an arc of rotation of the pins due to the offset portions of the sleeves.

In another broad form the present invention comprises:
a distraction and retraction assembly comprising;
first and second distraction pins;
sleeve members adapted to concentrically engage said pins for transmission of a distraction force to each pin;
a frame which receives and retains the sleeve members; the sleeve members each including an offset portion so that when a rotational load is applied to the sleeve members when said pins are inserted in vertebrae, the pins are capable of movement from a first position in which the vertebrae are in their natural position to a second position in which the vertebrae are distracted to a maximum extent;
the frame including means which receives and retains thereon retractor blades for retracting soft tissues.

According to a preferred embodiment the frame includes bridge formations which provide a mating engagement which allows at least rotational adjustment of said retractor blades.

The present invention provides an alternative to the known prior art and the shortcomings identified. The foregoing and other objects and advantages will appear from the description to follow. In the description reference is made to the accompanying representations, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying illustrations, like reference characters designate the same or similar parts throughout the several views. The following detailed description is, therefore, not to be taken in a limiting sense, and the scope of the present invention is best defined by the appended claims.

BRIEF DESCRIPTION OF THE DRAWINGS

FIG. 3 shows a fully assembled distraction and retraction assembly with anchor pins shown in a first position when vertebrae are not distracted.

FIG. 4 shows a the assembly of FIG. 3 with pins in a second disposition when vertebrae are fully distracted.

DETAILED DESCRIPTION

The present invention will now be described in more detail according to a preferred embodiment but non limiting embodiment and with reference to the accompanying illustrations.

The examples referred to herein are illustrative and are not to be regarded as limiting the scope of the invention. While various embodiments of the invention have been described herein, it will be appreciated that these are capable of modification, and therefore the disclosures herein are not to be construed as limiting of the precise details set forth, but to avail such changes and alterations as fall within the purview of the description.

To fully appreciate the various embodiments of the invention to be described below a summary of the bone fixation methodology and associated apparatuses and assemblies.

Figure 1:
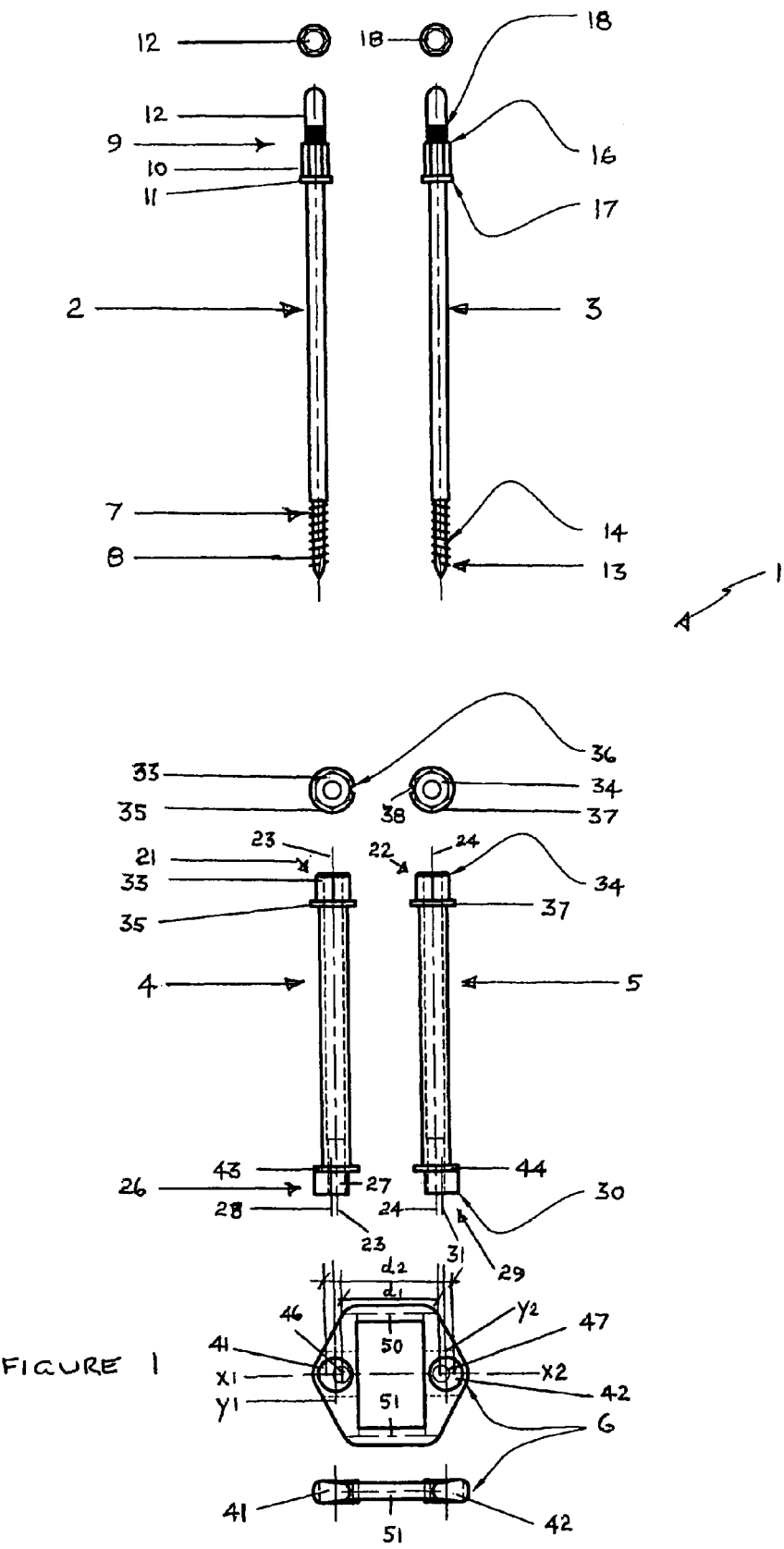
FIG. 1 shows an exploded view of a combined distraction and retraction assembly according to one embodiment.

FIG. 1 shows an exploded view of a distraction assembly which is capable of distracting bone components and which is able to receive and retain retractor blades to enable the assembly to provide combined distraction of bone and as required, retraction of soft tissues Assembly 1 is preferably adapted for distraction of spinal vertebrae and comprises, bone screw/anchor pins 2 and 3, concentric sleeves 4 and 5 and a frame 6. Pin 2 has a first end 7 with a threaded region 8 which when in situ engages spinal vertebrae (not shown). Opposite end 9 of pin 2 includes a hexagonal drive 10 adjacent flange 11 which provides an abutment surface which engages with sleeve 4 and allows pin 2 to be screwed axially into position in vertebral bone once pin 2 has been fed through sleeve 4. End 9 also includes a bone screw gripping region 12.

Likewise, anchor pin 3 has a first end 13 with a threaded region 14 which when in situ engages a spinal vertebrae (not shown). Opposite end 15 of pin 3 includes a hexagonal drive 16 adjacent flange 17 which provides an abutment surface for engagement with sleeve 5 and allows pin 3 to be screwed axially into position in vertebral bone once it has been fed through sleeve 5. End 13 also includes a bone screw gripping region 18.

Respective first ends 7 and 13 are respectively fed through sleeves 4 and 5 via respective proximal ends 21 and 22 such that the sleeves 4 and 5 concentrically surround pins 2 and 3 respectively. Pin 2 aligns with longitudinal axis 23 of sleeve 4 and pin 3 aligns with longitudinal axis 24 of concentric sleeve 5. At distal end 26 of sleeve 4 is an offset 27 whose longitudinal axis 28 is located eccentric to axis 23. Likewise, at distal end 29 of sleeve 5 is an offset 30 whose longitudinal axis 31 is located eccentric to axis 24. At proximal end 21 of sleeve 4 is a hexagonal formation 33 which is used for axial rotation of sleeve 4 when distraction and restoration of vertebra is required. Likewise, end 22 of sleeve 5 is a hexagonal formation 34 which is used for axial rotation of sleeve 5. End 21 also includes a flange 35 having a locating notch 36 and end 22 includes flange 37 having a locating notch 38.

Offset portion 27 aligns with opening 41 in frame 6 and offset 30 aligns with opening 42 in frame 6. Flange 43 on sleeve 4 provides an abutment surface which limits axial travel of sleeve 4 into circular opening 41. Flange 44 on sleeve 5 provides an abutment surface to limit axial travel of sleeve 5 into opening 42. It can be seen that axis 28 of offset 27 aligns with the intersection of orthogonal axes X1 and Y1 and axis 31 of offset portion 30 aligns with the intersection of orthogonal axes X2 and Y2. This leaves the anchor point of pin 2 shown by circle 46 eccentric to the intersection point of axes X1 Y1. Likewise anchor point of pin 3 shown by circle 47 is eccentric to the intersection point of axes X2 and Y2. Frame 6 includes bridges 50 and 51 which are capable of receiving and retaining retractor blades (not shown).

When the first ends 8 and 14 of each pin 2 and 3 are anchored in bone, axial rotation of each of sleeves 2 and 3 causes the said ends of each pin to move between a first position in which said vertebral bone is not distracted and a second position in which said vertebral bone is distracted. This may be achieved by clockwise or anticlockwise rotation of sleeves 4 and 5. In the first position when bone is not distracted the pins 2 and 3 are separated by distance d1. When pins 2 and 3 are at their maximum displacement they are separated by distance d2 when vertebral bones are distracted. Sleeves 4 and 5 can be rotated both in the clockwise direction at the same time or one clockwise and the other anti clockwise at the same time. The latter rotations may be preferable to minimise a component of opposite lateral vertebral displacement as the sleeves are rotated and the pins displace/distract the vertebra. Where one sleeve is rotated clockwise and the other anticlockwise both vertebra to which the pins are attached will undergo a small lateral displacement in the same lateral direction. Some distraction can be achieved by rotation of one only of either sleeves 4 or 5. Rotation of one sleeve alone may achieve sufficient distraction without need to rotate second sleeve.

According to one embodiment the pins 2 and 3 may be set in any position about a maximum arc of rotation between the first and second positions depending upon the degree of distraction of the vertebra required. Axial rotation of the sleeves translates to an arc of rotation of the pins due to the offset portions of the sleeves.

Figure 2:
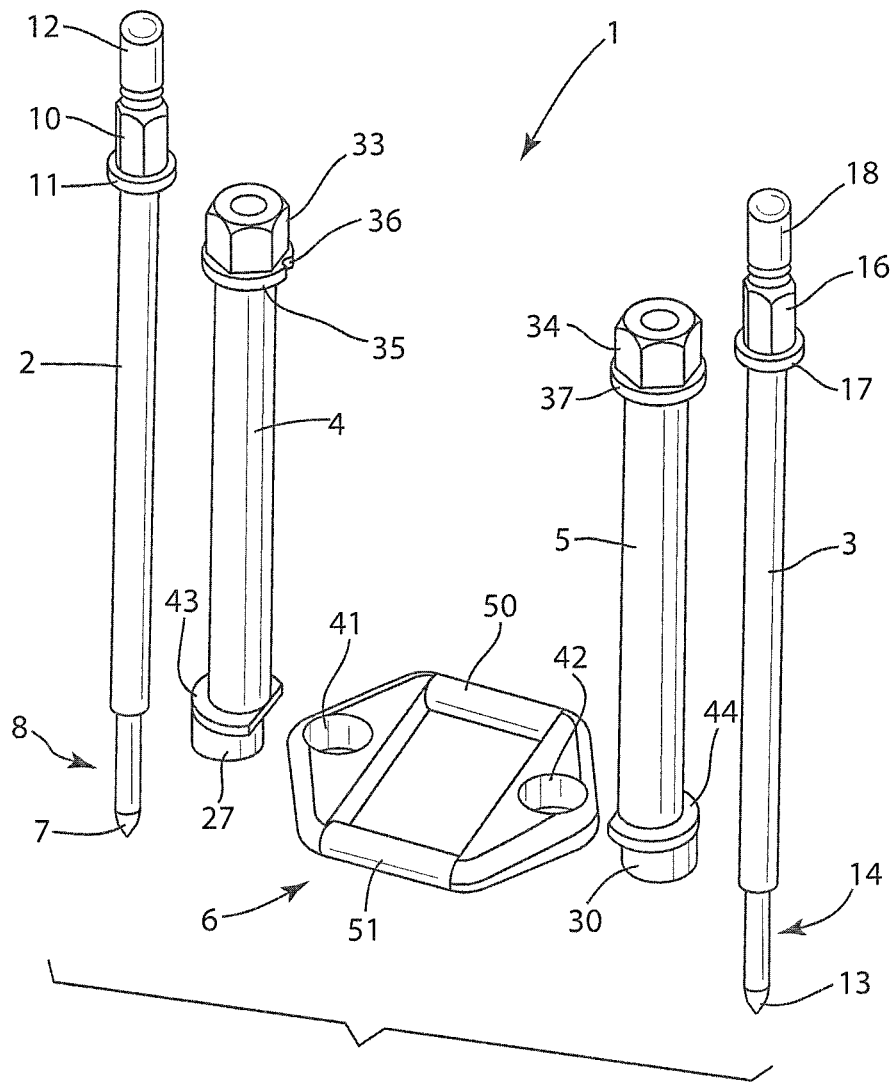
FIG. 2 shows an alternative exploded perspective view of the distraction and retraction assembly of FIG. 1.

FIG. 2 shows with corresponding numbering an alternative exploded perspective view of the distraction and retraction assembly 1 of FIG. 1.

FIG. 3 shows with corresponding numbering, the fully assembled distraction and retraction assembly with anchor pins 2 and 3 shown in a first position when vertebrae are not distracted at distance d1.

FIG. 4 shows a the assembly 1 of FIG. 3 with pins 2 and 3 in a second disposition when vertebrae are fully distracted to a distance d2. The extent of distraction distance can be incrementally selected by a surgeon at any position between d1 and d2. Comparing the arrangement of the distraction assembly of FIG. 3 with that of the assembly 1 of FIG. 4 it may be seen that sleeve 4 has been rotated 180 degrees from its position in FIG. 3 to its position in FIG. 4 thereby displacing pin 2 further away from pin 3. Likewise, it may be seen that sleeve 5 has been rotated 180 degrees from its position in FIG. 3 to its position in FIG. 4 thereby displacing pin 3 further away from pin 2. Thus rotation of sleeves 4 and 5 translates into an increase in a centre to centre distance between pins 2 and 3.

Although all embodiments show anchorage with bone being co-linear it is envisaged that anchorage pins or screws may be at an angle to the vertical.

It is common practice that after distraction of the vertebrae, prosthetic cages or bone graft are placed in the disc space with the intention that bone fusion occurs between the vertebrae. Such grafts or cages are usually slightly larger than the removed disc. After placement of graft or cage, the bones are often secured in position with screws either attached to plates or cages having screws running through them. It is a further object of this invention, that after distraction and insertion of interbody cage or bone graft, the invention can be used to apply compressive forces to the cage or bone graft prior to fixation of the bones with screws and plates. It can be understood by persons skilled in the art that the same mechanism that effects distraction of the vertebrae may also be used to return bones to their original position. If this is done after insertion of a bone graft or cage (which is normally slightly larger than original space) into the intervertebral space then compression forces will be applied to the graft. If the bones now held in compression are then secured in position with screws or some other mechanism prior to removal of device then the graft will be held under compression. This is advantageous. Such compression forces should preferably be applied with rotation of sleeves in opposite direction to ensue no relative lateral shift of vertebrae prior to permanent fixation with screws or other method. "After distraction and after placement of interbody graft or cage (larger than original disc space) into the intervertebral space, rotation of the sleeves back to their starting position will create a compression of the cage or graft between the vertebrae."

The assembly herein described can be manufactured from a variety of materials such as but not limited to metals and plastics. The assembly can be manufactured as a disposable item or re usable. In the latter case the material selected must be capable of sterilisation.

It will be appreciated by those skilled in the art that the utilisation of this principal could be used in numerous other applications adapting to the different anatomy and retraction requirements throughout the spine, musculoskeletal system or wherever bony fixation can be utilised, e.g. the head.

It will be further recognised by persons skilled in the art that numerous variations and modifications may be made to the invention without departing from the overall spirit and scope of the invention broadly described herein. Such modifications would allow adaptation of key concepts to provide additional distraction for use in anterior or posterior spinal surgery throughout the length of spine or in orthopaedics or other surgical disciplines where bony fixation is available.

The invention claimed is:

1. An assembly for distraction of spinal vertebrae, the assembly comprising:
   first and second pins each having a distal end adapted for vertebral bone engagement, a second end, and a concentric sleeve connected thereto; and
   a frame including respective openings which receive the pins and a distal end of each of said sleeves, and
   wherein the distal end of each of said concentric sleeves includes a portion offset relative to a longitudinal axis of said concentric sleeve such that, when the distal end of each said pins is anchored in vertebral bone, axial rotation of said concentric sleeves enables said distal end of each of said pins to move between a first position in which said vertebral bone is not distracted and a second position in which said vertebral bone is distracted.

2. An assembly according to claim 1, wherein the offset portion of each concentric sleeve engages one of said respective openings in said frame such that a longitudinal axis of a respective pin of the first and second pins for the concentric sleeve is offset relative to an axis through said offset portion.

3. An assembly according to claim 2, wherein, as each of said concentric sleeves is rotated, the distal end of the respective pin for the concentric sleeve defines an arc of rotation about the axis through said offset portion of the concentric sleeve thereby applying a distraction force to said respective pin via said concentric sleeve.

4. An assembly according to claim 3, wherein the frame includes bridging members which are capable of receiving and retaining at least one retractor blade.

5. An assembly according to claim 4, wherein the first pin extends from an anchor point to a proximal end of the respective concentric sleeve for the first pin and the second pin extends from an anchor point to a proximal end of the respective concentric sleeve for the second pin.

6. An assembly according to claim 5, wherein a proximal end of each of the first and second pins comprises a hexagonal nut that extends beyond the proximal end of the respective concentric sleeve for the pin when the concentric sleeve is fully engaged with the pin.

7. An assembly according to claim 6, wherein the hexagonal nut of each pin is configured to receive a tool that enables rotation of the respective concentric sleeve for the pin.

8. An assembly according to claim 7, wherein the offset portion of each of the concentric sleeves includes a cam surface that cooperates with a surface in the respective openings in the frame during rotation of the concentric sleeve.

9. An assembly according to claim 8, wherein, when the respective concentric sleeve for each pin is concentrically mounted about the pin, the longitudinal axis of pin is coincident with the longitudinal axis of the respective concentric sleeve for the pin.

10. An assembly according to claim 9, wherein, for each of the first and second pins, the axis through the offset portion of the respective concentric sleeve for the pin is parallel to but offset from the longitudinal axis of the pin.

11. An assembly according to claim 10, wherein the offset portions of the respective concentric sleeves for the first and second pins allow the pins to undergo an arcuate displacement upon rotation of the concentric sleeves causing axial displacement of the pins.

12. An assembly according to claim 11, wherein the frame includes spaced apart abutment members having the respective openings.

13. An assembly according to claim 12, wherein the abutment members are joined by first and second bridging members.

14. An assembly according to claim 13, wherein the proximal end of each of the first and second pins includes a gripping region.

15. An assembly according to claim 14, wherein the distal end of each of the first and second pins includes a helical thread which enables anchorage of the pin.

16. An assembly according to claim 15, wherein, when the respective concentric sleeve for each pin is concentrically mounted about the pin, the hexagonal nut at the proximal end of the pin includes a flange that engages a hex nut at the proximal end of the respective concentric sleeve for the pin.

17. An assembly allowing distraction of adjacent spinal vertebrae, the assembly comprising:
   a pair of anchor pins each having a first distal end that is capable of engagement with respective vertebrae,
   a pair of sleeves that respectively and concentrically engage the anchor pins; and a frame including two openings each receiving one of the sleeves via an offset portion of the sleeve received by the opening, and wherein the offset portion of each sleeve locates a longitudinal axis through the anchor pin respectively engaged by the sleeve in an offset position relative to a central axis through the offset portion of the sleeve thereby allowing the distal ends of the anchor pins to move between a first position of minimum pin separation in which the vertebrae are in an undistracted position and a second position of maximum pin separation in which the vertebrae are distracted to a maximum extent, and wherein, due to the offset portion of the sleeves, axial rotation of the sleeves translates to displacement of the anchor pins such that the anchor pins distract the vertebrae to an extent that is determined by rotation of the sleeves.

18. A distracter assembly, comprising:
a first pin that is capable of anchorage in vertebral bone via a distal end of the first pin;
a first sleeve that is mountable concentrically with the first pin;
a second pin that is capable of anchorage in vertebral bone via a distal end of the second pin;
a second sleeve that is mountable concentrically with the second pin; and
a base member that receives the first and second pins and retains the first and second sleeves, and
wherein the first and second sleeves each include a cam surface that cooperates with a surface on the base member such that, upon rotation of the first and second sleeves, the first and second pins displace thereby displacing the bone in which the first and second pins are anchored.

* * * * *